United States Patent
Xu et al.

(10) Patent No.: US 9,328,097 B2
(45) Date of Patent: May 3, 2016

(54) THERMALLY ACTIVATED DELAYED FLUORESCENCE MATERIAL, A METHOD OF SYNTHESIZING THE SAME AND AN OLED DEVICE USING THE SAME

(71) Applicant: Shenzhen China Star Optoelectronics Technology Co., Ltd., Shenzhen, Guangdong (CN)

(72) Inventors: Shidang Xu, Shenzhen (CN); Zhenguo Chi, Shenzhen (CN); Yi Zhang, Shenzhen (CN); Jiarui Xu, Shenzhen (CN); Yifan Wang, Shenzhen (CN); Qinghua Zou, Shenzhen (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 136 days.

(21) Appl. No.: 14/345,939

(22) PCT Filed: Jan. 23, 2014

(86) PCT No.: PCT/CN2014/071163
§ 371 (c)(1),
(2) Date: Mar. 19, 2014

(87) PCT Pub. No.: WO2015/096260
PCT Pub. Date: Jul. 2, 2015

(65) Prior Publication Data
US 2015/0280138 A1    Oct. 1, 2015

(51) Int. Cl.
| | |
|---|---|
| *C07D 209/86* | (2006.01) |
| *C07D 403/12* | (2006.01) |
| *C07D 417/10* | (2006.01) |
| *C07D 403/10* | (2006.01) |
| *C07D 403/14* | (2006.01) |
| *C09K 11/06* | (2006.01) |
| *C07D 279/22* | (2006.01) |
| *H01L 51/00* | (2006.01) |
| *H01L 51/50* | (2006.01) |

(52) U.S. Cl.
CPC ............ *C07D 403/12* (2013.01); *C07D 209/86* (2013.01); *C07D 279/22* (2013.01); *C07D 403/10* (2013.01); *C07D 403/14* (2013.01); *C07D 417/10* (2013.01); *C09K 11/06* (2013.01); *H01L 51/0052* (2013.01); *H01L 51/0056* (2013.01); *H01L 51/0058* (2013.01); *H01L 51/0067* (2013.01); *H01L 51/0071* (2013.01); *H01L 51/0072* (2013.01); *H01L 51/0074* (2013.01); *H01L 51/5012* (2013.01); *C09K 2211/1007* (2013.01); *C09K 2211/1011* (2013.01); *C09K 2211/1014* (2013.01); *C09K 2211/1029* (2013.01); *C09K 2211/1037* (2013.01); *C09K 2211/1051* (2013.01); *C09K 2211/1059* (2013.01); *H01L 51/5056* (2013.01); *H01L 51/5072* (2013.01); *H01L 2251/552* (2013.01)

(58) Field of Classification Search
CPC .. C07D 209/86; C07D 403/12; C07D 417/10; C07D 403/10; C07D 403/14
See application file for complete search history.

(56) References Cited

FOREIGN PATENT DOCUMENTS

| | | |
|---|---|---|
| CN | 101343537 A | 1/2009 |
| CN | 103483332A A | 1/2014 |
| CN | 103694992A A | 4/2014 |
| JP | 2008163190A A | 7/2008 |

OTHER PUBLICATIONS

Liu et al. Chem. Eur. J. 2012, 18, 9929-9938.*
Hong et al. Chem. Soc. Rev. 2011, 40, 5361-5388.*

* cited by examiner

*Primary Examiner* — Matthew Coughlin
(74) *Attorney, Agent, or Firm* — Andrew C. Cheng (57) ABSTRACT

The present invention provides a thermally activated delayed fluorescence material, a method of synthesizing the same and an OLED device using the same. The thermally activated delayed fluorescence material includes a structure formula 1 as Ar—$(Ar1)_m$-$(Ar2)_n$, wherein the number of m is in 1~4, the number of n is in 1~8, the group Ar is an electron withdrawing group, the group Ar1 is an electron donating group and the group Ar2 is an aggregation induced emission group. The thermally activated delayed fluorescence material has a higher glass transition temperature, high thermal stability and excellent luminous efficiency. The method of synthesizing the same has simplified steps, easily purified product, high yield, and luminous and thermal properties of the product can be adjusted by connecting to differentiated functional groups.

1 Claim, 2 Drawing Sheets

THERMALLY ACTIVATED DELAYED FLUORESCENCE MATERIAL, A METHOD OF SYNTHESIZING THE SAME AND AN OLED DEVICE USING THE SAME

FIELD OF THE INVENTION

The present invention relates to a thermally activated delayed fluorescence material, a method of synthesizing the same and an OLED device using the same; and more particularly relates to a thermally activated delayed fluorescence (TADF) material having aggregation induced emission (AIE) property, a method of synthesizing the same and an OLED device using the same.

BACKGROUND OF THE INVENTION

Due to great potential application to flexible display devices etc., the organic light emitting diode (OLED) device is attached great importance by the scientific community and display industry in recent years, and it is one of the hot spots of current research and development.

However, the OLED device technology is currently experiencing a bottleneck in the development process; a main issue is that light emitting efficiency and lifetime of the OLED device cannot meet practical demand so as to greatly limit the development of the OLED technology. Factors of affecting the luminous efficiency and service life of the OLED device are multifaceted, but the fluorescence efficiency and stability of the light emitting material directly affect the performance of the OLED device. Most of dilute solutions of the light emitting materials have a high fluorescence quantum yield; however, they become weak fluorescence or not luminous in solid state. The phenomenon of the light emitting materials comes from aggregation caused quenching (ACQ). In general, the light emitting materials shall be used in solid thin film state; therefore, the ACQ effect inevitably occurs.

In order to reduce concentration of a light emitting material so as to resolve the ACQ effect, most of the light emitting materials are prepared with physically doping methods. There are many drawbacks in the physically doping methods, for example, to control the ratio between subject and object of the light emitting materials in the vacuum deposition process is difficult; phase separation exists between subject and object thereof; and processes of the physically doping method are complicated. If there is a light emitting material, the more it is aggregated, the stronger luminescence and the higher fluorescence quantum it yields, the ACQ effect would be possibly solved with the light emitting material. Such a light emitting material is called aggregation induced emission (AIE) material. Since 2001 Ben Zhong Tang et. al. reported that silacyclopentadiene derivatives (Silole) have the AIE effect, the AIE materials have been aroused great attention. With light emitting efficiency of the AIE materials in solid state being much better than light emitting efficiency thereof in solution state, a way to overcome the problem of doping organic light emitting materials is provided.

A fluorescence material doped with metal complex has a high light emitting efficiency with triplet state excitons in which green light material and red light material in the light emitting material can meet the demand of luminescence; however, the metal complex doped therein has specific structure of electrons so that blue light material therein cannot meet the demand of luminescence. Therefore, a thermally activated delayed fluorescence (TADF) material having properties between fluorescence and phosphorescence greatly increases light emitting efficiency of the fluorescence material, which is almost same as light emitting efficiency of a phosphorescence material, to make up shortage of the blue phosphorescent materials. Due to the ACQ effect existed in the known TADF material, an OLED device using the known TADF material can be only fabricated with the doping method. Therefore, it is one way of resolving the above said problems to develop a new light emitting material having the properties of the AIE material and the TADF material.

SUMMARY OF THE INVENTION

In accordance with an aspect, the present invention provides a thermally activated delayed fluorescence material. The thermally activated delayed fluorescence material has the property of aggregation induced emission (AIE) so as to have a higher glass transition temperature, high thermal stability and excellent luminous efficiency.

In accordance with another aspect, the present invention provides a method of synthesizing the thermally activated delayed fluorescence material having the property of AIE. The method of synthesizing the same has simplified steps, easily purified product, high yield, and luminous and thermal properties of the product can be adjusted by connecting to differentiated functional groups.

In accordance with another aspect, the present invention provides an OLED device using the thermally activated delayed fluorescence material having the property of AIE. The OLED device using the same has a light emitting layer of high fluorescence efficiency and long-term stability, so that luminous efficiency and service life of the OLED device can meet practical demand.

For the above aspects, the present invention provides a thermally activated delayed fluorescence material including a structure formula 1 as Ar—(Ar1)$_m$-(Ar2)$_n$, wherein the number of m is in 1~4, the number of n is in 1~8, the group Ar is an electron withdrawing group, the group Ar1 is an electron donating group is and the group Ar2 is an aggregation induced emission group.

In an embodiment, the group Ar selected from the following structure formulas:

-continued

In an embodiment, the group Ar1 is selected from the following structure formulas:

In an embodiment, the group Ar2 is selected from the following structure formulas:

-continued

For the above aspects, the present invention provides a method of synthesizing the thermally activated delayed fluorescence material. The thermally activated delayed fluorescence material includes a structure formula 1 as Ar—(Ar1)$_m$ (Ar2)$_n$, wherein the number of m is in 1~4, the number of n is in 1~8, the group Ar is an electron withdrawing group, the group Ar1 is an electron donating group and the group Ar2 is an aggregation induced emission group. The method includes steps as follows.

Step 1, a halide of the group Ar1 and a halide of the group Ar2 are provided, and a boric acid or borate corresponding to one of the halide of the group Ar1 and the halide of the group Ar2 is prepared.

Step 2, a coupling reaction of the boric acid or borate prepared in Step 1 and the other one of the halide of the group Ar1 and the halide of the group Ar2 is performed to form a substituted aromatic amine.

Step 3, a halide of the group Ar is provided, and the halide of the group Ar reacts with the substituted aromatic amine to form the thermally activated delayed fluorescence material.

In an embodiment, the group Ar1 is selected from the following structure formulas:

and the halide of the group Ar1 is a monohalogenated or dihalogenated compound, the monohalogenated or dihalogenated compound is a bromo compound or iodo compound.

In an embodiment, the halide of the group Ar1 is bromo carbazole, iodo carbazole, bromoo phenothiazine, iodo phenothiazine, bromo diphenylamine or iodo diphenylamine.

In an embodiment, the group Ar2 is selected from the following structure formulas:

and the halide of the group Ar2 is a halide including triphenylethylene tetraphenylethylene, the halide including triphenylethylene tetraphenylethylene is a bromo compound or iodo compound.

In an embodiment, the group Ar is selected from the following structure formulas:

and the group Ar is a fluoro compound, bromo compound or iodo compound.

For the above aspect, the present invention provides an OLED device using the thermally activated delayed fluorescence. The OLED device using the same includes a substrate, a transparent conductive layer, a hole transport layer, a light emitting layer, an electron transport layer and a metal layer. The transparent conductive layer is formed on the substrate. The hole transport layer is formed on the transparent conductive layer. The light emitting layer is formed on the hole transport layer. The electron transport layer is formed on the light emitting layer. The metal layer is formed on the electron transport layer. The light emitting layer includes a thermally activated delayed fluorescence material including a structure formula 1 as Ar—(Ar1)$_m$-(Ar2)$_n$, wherein the number of m is in 1~4, the number of n is in 1~8, the group Ar is an electron withdrawing group, the group Ar1 is an electron donating group is and the group Ar2 is an aggregation induced emission group.

According to the present invention, the thermally activated delayed fluorescence material overcomes the ACQ effect of known thermally activated fluorescence materials and has the AIE property so as to have a higher glass transition temperature, high thermal stability and excellent luminous efficiency. The method of synthesizing the same has simplified steps, easily purified product, high yield, and luminous and thermal properties of the product can be adjusted by connecting to differentiated functional groups. The OLED device using the same has a light emitting layer of high fluorescence efficiency and long-term stability, so that luminous efficiency and service life of the OLED device can meet practical demand.

BRIEF DESCRIPTION OF THE DRAWINGS

The above objects and advantages of the present invention will become more readily apparent to those ordinarily skilled in the art after reviewing the following detailed description and accompanying drawings, in which.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

The present invention provides a thermally activated delayed fluorescence material. The thermally activated delayed fluorescence material includes a structure formula 1 as Ar—(Ar1)$_m$-(Ar2)$_n$, wherein the number of m is in 1~4, the number of n is in 1~8, the group Ar is an electron withdrawing group, the group Ar1 is an electron donating group is and the group Ar2 is an aggregation induced emission group.

In an embodiment, the group Ar selected from the following structure formulas:

In an embodiment, the group Ar1 is selected from the following structure formulas:

In an embodiment, the group Ar2 is selected from the following structure formulas:

or

Figure 1:
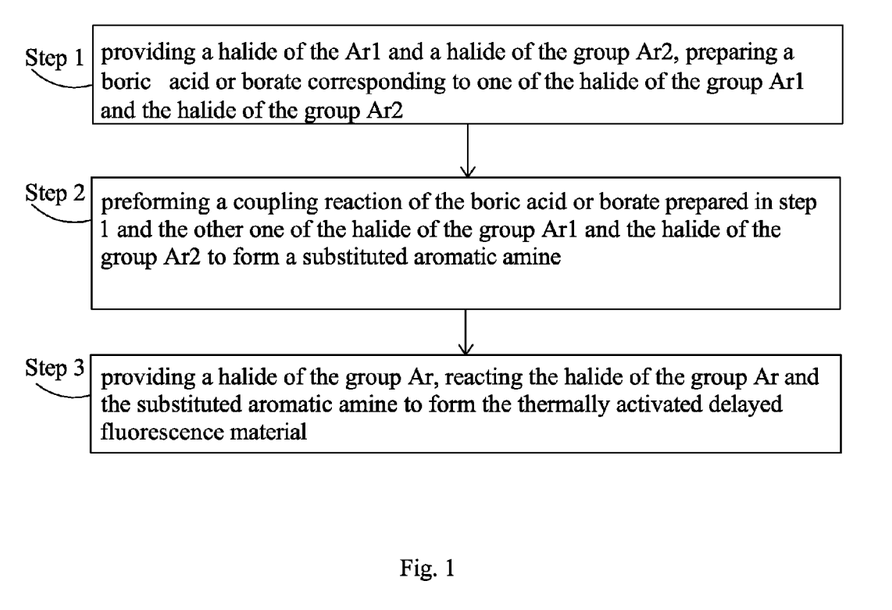
FIG. 1 is a flow chart illustrating a method of synthesizing a thermally activated delayed fluorescence material according to an embodiment of the present invention.

FIG. 1 is a flow chart illustrating a method of synthesizing a thermally activated delayed fluorescence material according to an embodiment of the present invention. The thermally activated delayed fluorescence material includes a structure formula 1 as Ar—(Ar1)$_m$-(Ar2)$_n$, wherein the number of m is in 1~4, the number of n is in 1~8, the group Ar is an electron withdrawing group, the group Ar1 is an electron donating group and the group Ar2 is an aggregation induced emission group. Please refer to FIG. 1, the method includes steps as follows:

Step 1, providing a halide of the group Ar1 and a halide of the group Ar2, and preparing a boric acid or borate corresponding to one of the halide of the group Ar1 and the halide of the group Ar2.

In Step 1, the group Ar1 is an electron donating group, such as carbazole group, selected from the following structure formulas:

and the halide of the group Ar1 is a monohalogenated or dihalogenated compound, the monohalogenated or dihalogenated compound is a bromo compound or iodo compound, for example, the halide of the group Ar1 is bromo carbazole, iodo carbazole, bromoo phenothiazine, iodo phenothiazine, bromo diphenylamine or iodo diphenylamine; and the group Ar2 is an aggregation induced emission group, such as tetraphenylethylene, selected from the following structure formulas:

and the halide of the group Ar2 is a halide including triphenylethylene tetraphenylethylene, the halide including triphenylethylene tetraphenylethylene is a bromo compound or iodo compound. The halogen elements in the halide of the group Ar1 or the halide of the group Ar2 are converted to the boric acid or borate by reacting the halide of the group Ar1 or halide of the group Ar2 so that the boric acid or borate corresponding to the halide of the group Ar1 or the halide of the group Ar2 is prepared. In this step, the halide of the group Ar1 is selected to be reacted, the halide of the group Ar2 do not need to be processed; similarly, the halide of the group Ar2 is selected to be reacted, the halide of the group Ar2 do not need to be processed.

Step 2, preforming a coupling reaction of the boric acid or borate prepared in Step 1 and the other one of the halide of the group Ar1 and the halide of the group Ar2 to form a substituted aromatic amine.

In Step 2, the coupling reaction is the Suzuki coupling reaction, and the substituted aromatic amine is formed after the reaction is performed.

Step 3, providing a halide of the group Ar, reacting the halide of the group Ar and the substituted aromatic amine to form the thermally activated delayed fluorescence material.

In Step 3, the group Ar is selected from the following structure formulas:

and the group Ar is a fluoro compound, bromo compound or iodo compound.

In practical preparation, the structure of the group Ar, the group Ar1 and the group Ar2 can be selected as needed, and the properties of the thermally activated delayed fluorescence, such as light emitting and thermal stability, can be adjusted by connecting to differentiated functional group.

The method of synthesizing the thermally activated delayed fluorescence material according to the present invention will now be elaborated more specifically with reference to, but not limited to, the following embodiments.

Embodiment 1

A synthesis of 4,4'-bis[3,6-bis(triphenyl vinyl)]carbazolyl diphenyl sulfone

1. A synthesis of tristyryl boronate 167.62 g bromo tristyrene (0.5 mol), 126.97 g diboron pinacol ester (0.5 mol) and 29.44 g potassium acetate (0.3 mol) are taken and placed into a three-necked flask, 300 mL dioxane is added, an amount of catalyt Pd(dppf)Cl$_2$ is added under argon protection, and the reactants are stirred to react for 24 hours at room temperature. The product solution is extracted with water and dichloromethane, the organic phase is evaporated by the rotary evaporation under reduced pressure, then separated and purified by the column chromatography, and the product (85% yield) is obtained. A route of synthesizing tristyryl boronate is shown as following formula 2:

2. A synthesis of bis(triphenylethylene) substituted carbazole 76.46 g triphenylethylene borate (0.2 mol), 32.50 g 3,6-dibromo carbazole (0.1 mol) are taken and placed into a three-necked flask, 20 mL toluene, 5 mL K$_2$CO$_3$ (2M solution) and 1 g TBAB (tetrabutyl bromide) are added, the reactants are stirred under argon for 30 minutes, an amount of Pd(dppf)Cl$_2$ is added, and the three-necked flask accommodating the reactants is put in oil bath and heated to react at 90° C. for 24 hours. After the reaction is completed, the product solution is extracted with water and dichloromethane, organic phase of the extracted solution is dried with anhydrous sodium sulfate, and a crude product is obtained through a vacuum rotary drying process with a rotary evaporator, the crude product is purified by using silica gel column chromatography with a mixed solution of n-hexane and dichloromethane (a certain volume ratio) as an eluent, and a pure product is obtained (70% yield). A route of synthesizing bis(triphenylethylene) substituted carbazole is shown as following formula 3:

3. A synthesis of final product of 4,4'-bis[3,6-bis(triphenyl vinyl)]carbazolyl diphenyl sulfone 13.52 g bis(triphenylethylene) substituted carbazole (0.02 mol) and 2.54 g 4,4'-difluoro diphenyl sulfone (0.01 mol) are taken and placed into a three-necked flask, 100 mL DMF (N,N-dimethyl formamide) and 2.24 g potassium t-butoxide (0.002 mol) are added, the reactants are stirred under argon and heated to react at 90° C. for 24 hours. After the reaction is completed, the product solution is extracted with water and dichloromethane, organic phase of the extracted solution is dried with anhydrous sodium sulfate, and a crude product is obtained through a vacuum rotary drying process with a rotary evaporator, the crude product is purified by using silica gel column chromatography with a mixed solution of n-hexane and dichloromethane (a certain volume ratio) as an eluent, and a pure product is obtained (89% yield). A route of synthesizing 4,4'-bis[3,6-bis(triphenyl vinyl)]carbazolyl diphenyl sulfone is shown as following formula 4:

-continued i.e. a structure formula of $(Ar2)_2$-$(Ar1)$-$Ar$—$(Ar1)$-$(Ar2)_2$.

Embodiment 2

A synthesis of 4,4'-bis(3-triphenylethylene) carbazolyl diphenyl sulfone

According to Step 2 of Embodiment 1, mono-triphenylethylene substituted carbazole is obtained, wherein the halgeno carbazole is 3-bromo carbazole; and according to Step 3 of Embodiment 1, a final product of 4,4'-bis(3-triphenylethylene) carbazolyl diphenyl sulfone is obtained (82% yield). A route of synthesizing 4,4'-bis(3-triphenylethylene) carbazolyl diphenyl sulfone is shown as following formula 5:

i.e. a structure formula of (Ar2)-(Ar1)-Ar—(Ar1)-(Ar2).

Embodiment 3

A synthesis of 4,4'-bis(3-tetraphenylethylene) carbazolyl diphenyl sulfone

According to Step 1 of Embodiment 1, tetraphenylethylene borate is obtained; according to Step 2 of Embodiment 1, mono-tetraphenylethylene substituted carbazole is obtained, wherein the halgeno carbazole is 3-bromo carbazole; and according to Step 3 of Embodiment 1, a final product of 4,4'-bis(3-tetraphenylethylene) carbazolyl diphenyl sulfone is obtained (80% yield). A route of synthesizing 4,4'-bis(3-tetraphenylethylene) carbazolyl diphenyl sulfone is shown as following formula 6.

i.e. a structure formula of (Ar2)-(Ar1)-Ar—(Ar1)-(Ar2).

Embodiment 4

A synthesis of 1,3,5-tris[3,6-bis(triphenyl vinyl)]carbazolyl triazine 20.28 g bis(triphenylethylene) substituted carbazole obtained in Step 2 of Embodiment 1 is dissolved in 100 mL Of anhydrous THF, 14 mL 2.5M n-butyl lithium (0.035 mol) is dropped at 0° C., then, 20 mL solution of 1.841 g cyanuric chloride (0.01 mol) dissolved in THF is dropped, and the reactants are heated to react at 70° C. for 24 hours. After the reaction is completed, the product solution is extracted with water and dichloromethane, organic phase of the extracted solution is dried with anhydrous sodium sulfate, and a crude product is obtained through a vacuum rotary drying process with a rotary evaporator, the crude product is purified by using silica gel column chromatography with a mixed solution of n-hexane and dichloromethane (a certain volume ratio) as an eluent, and a pure product is obtained (68% yield). A route of synthesizing 1,3,5-tris[3,6-bis(triphenyl vinyl)]carbazolyl triazine is shown as following formula 7:

i.e. a structure formula of Ar—(Ar1)$_3$-(Ar2)$_6$.

Embodiment 5

A synthesis of 4,4'-bis(3-triphenylethylene phenothiazine)yl diphenyl ketone Please refer to the synthesizing method of Embodiment 3, an intermediate of mono-tetraphenylethylene substituted carbazole is obtained; then, according to Step 3 of Embodiment 1, a final product is formed by reacting the intermediate with 4,4'-difluoro benzophenone (78% yield). A route of synthesizing 4,4'-bis(3-triphenylethylene phenothiazine)yl diphenyl ketone is shown as following formula 8:

i.e. a structure formula of (Ar2)-(Ar1)-Ar—(Ar1)-(Ar2).

Embodiment 6

A synthesis of 2,2'-biscyano-7,7'-bis[3,6-bis(triphenylvinyl)]carbazolyl-9,9'-spirobifluornyl

Using an intermediate of 13.52 g bis(triphenylethylene) carbazole (0.02 mol) obtained in Embodiment 1 to react with a solution of 6.18 g dicyano difurazanyl iodine spirofluorene (0.01 mol) dissolved in 100 mL DMF, the reaction thereof is performed by using a catalyst of cuprous oxide at 100° C. for 24 hours. After the reaction is completed, the product solution is extracted with water and dichloromethane, organic phase of the extracted solution is dried with anhydrous sodium sulfate, and a crude product is obtained through a vacuum rotary drying process with a rotary evaporator, the crude product is purified by using silica gel column chromatography with a mixed solution of n-hexane and dichloromethane (a certain volume ratio) as an eluent, and a pure product is obtained (58% yield). A route of synthesizing 2,2'-biscyano-7,7'-bis[3,6-bis(triphenylvinyl)]carbazolyl-9,9'-spirobifluornyl is shown as following formula 9:

i.e. a structure formula of $(Ar2)_2$-$(Ar1)$-$Ar$—$(Ar1)$-$(Ar2)_2$.

Control Embodiment 1

Firstly, 3.34 g carbazole (0.02 mol), 2.55 g 4,4'-difluoro diphenyl sulfone (0.01 mol) are taken and placed into a three-necked flask, 100 mL N, N-dimethyl formamide (DMF) and 2.24 g potassium tert-butoxide (0.02 mol) are added into the three-necked flask, stirred and poured with argon, and the reactants are heated to react at 90° C. for 24 hours. After the reaction is completed, the solution is extracted with water and dichloromethane, organic phase of the extracted solution is dried with anhydrous sodium sulfate, and a crude product is obtained through a vacuum rotary drying process with a rotary evaporator. Then, the crude product is purified by using silica gel column chromatography with a mixed solution of n-hexane and dichloromethane (a certain volume ratio) as an eluent. Then, a product is obtained (85% yield). A route of Control Embodiment 1 is shown as following formula 10.

Control Embodiment 2

With reference to the synthesizing method of Control Embodiment 1, a yield of Control Embodiment 2 is 82%, and a route of Control Embodiment 2 is shown as following formula 11.

For further describing performance of the thermally activated delayed fluorescence material according to the present invention, a property test of the products (i.e. target compounds) of Embodiments 1-4 is performed. The main items in the property test are thermal property and maximum fluorescence emission wavelength, and the test results are shown in Table 1.

TABLE 1

| compound | Tg (° C.) | Td (° C.) | $\lambda_{max}^{em}$ (nm) | $\Phi_F$ |
|---|---|---|---|---|
| Embodiment 1 | 201.3 | 413.2 | 498 | 75.8% |
| Embodiment 2 | 195.2 | 421.3 | 489 | 56.5% |
| Embodiment 3 | 198.2 | 482.1 | 495 | 96.5% |
| Embodiment 4 | 270.1 | 490.2 | 501 | 76.5% |
| Embodiment 5 | 143.1 | 415.3 | 525 | 92.8% |
| Embodiment 6 | 256.4 | 481.6 | 545 | 78.3% |
| Control Embodiment 1 | 125.2 | 321 | 419 | 32.1% |
| Control Embodiment 2 | 130.3 | 333 | 408 | 25.4% |

In the property test, the test of weight loss temperature Td is measured at 1% weight loss in 20 mL/min nitrogen by using a thermal analyzer (TGA-50H, Shimadzu Corp., Japan); the test of glass transition temperature Tg is measured with a differential scanning calorimetry (DSC) by using a differential scanning calorimeter (DSC204F1, NETZSCH company, German) at 10° C./min heating rate; the test of maximum fluorescence emission wavelength $\lambda_{max}^{em}$ of powder sample uses a fluorescence spectrophotometer (RF-5301pc, Shimadzu Corp., Japan); the test of fluorescence quantum efficiency $\Phi_F$ of powder sample uses a fiber optic spectrometer (a solid fluorescence quantum efficiency test system consisted of Maya 2000Pro, U.S. Ocean Optics, American Blue Philippine's C-701 integrating sphere and U.S. Ocean Optics LLS-LED light source, according to a test method disclosed in the literature Adv. Mater. 1997, Method 9, 230-232).

Based on the results in Table 1, the thermally activated delayed fluorescence material according to the present invention has a better thermal stability, higher glass transition temperature and stronger luminous intensity. Therefore, the thermally activated delayed fluorescence material according to the present invention is very suitable for use of forming an undoped light emitting layer material in OLED devices; also, adapted to technique fields related to chemical, biological and pressure sensors.

Figure 2:
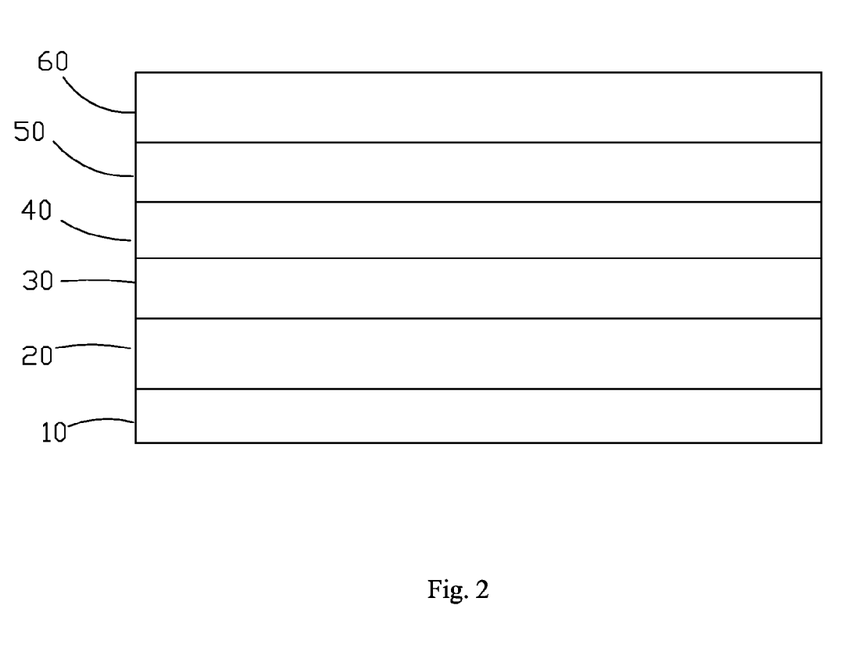
FIG. 2 is a schematic cross-section view illustrating an OLED device using a thermally activated delayed fluorescence material according to the present invention.

For the above aspect, the present invention provides an OLED device using the thermally activated delayed fluorescence. FIG. 2 is a schematic cross-section view illustrating an OLED device using a thermally activated delayed fluorescence material according to the present invention. Please refer to FIG. 2, the OLED device using the same includes a substrate 10, a transparent conductive layer 20, a hole transport layer 30, a light emitting layer 40, an electron transport layer 50 and a metal layer 60. The transparent conductive layer 20 is formed on the substrate 10. The hole transport layer 30 is formed on the transparent conductive layer 20. The light emitting layer 40 is formed on the hole transport layer 30. The electron transport layer 50 is formed on the light emitting layer 40. The metal layer 60 is formed on the electron transport layer 50. The light emitting layer 40 includes a thermally activated delayed fluorescence material as an undoped light emitting material of the light emitting layer 40.

In conclusion, the thermally activated delayed fluorescence material according to the present invention overcomes the ACQ effect of known thermally activated fluorescence materials and has the AIE property so as to have a higher glass transition temperature, high thermal stability and excellent luminous efficiency. The method of synthesizing the same has simplified steps, easily purified product, high yield, and luminous and thermal properties of the product can be adjusted by connecting to differentiated functional groups. The OLED device using the same has a light emitting layer of high fluorescence efficiency and long-term stability, so that luminous efficiency and service life of the OLED device can meet practical demand.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:
1. A thermally activated delayed fluorescence material, comprising a molecular structure formula 1 as Ar—(Ar1)$_m$-(Ar2)$_n$, wherein the number of m is in 1~4, the number of n is in 1~8, the group Ar is an electron withdrawing group, the group Ar1 is an electron donating group and the group Ar2 is an aggregation induced emission group, wherein the group Ar is selected from the following structure formulas:

the group Ar1 is selected from the following structure formulas:

the group Ar2 is selected from the following structure formulas:

* * * * *